United States Patent
Wang et al.

(10) Patent No.: US 11,559,606 B2
(45) Date of Patent: Jan. 24, 2023

(54) SEMI-SYNTHETIC TISSUE CONSTRUCTS FOR TISSUE REGENERATION

(71) Applicant: The Penn State Research Foundation, University Park, PA (US)

(72) Inventors: Yong Wang, State College, PA (US); Xiaolong Zhang, Downingtown, PA (US); Nan Zhao, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 854 days.

(21) Appl. No.: 16/467,104

(22) PCT Filed: Dec. 11, 2017

(86) PCT No.: PCT/US2017/065549
§ 371 (c)(1),
(2) Date: Jun. 6, 2019

(87) PCT Pub. No.: WO2018/107148
PCT Pub. Date: Jun. 14, 2018

(65) Prior Publication Data
US 2019/0351100 A1  Nov. 21, 2019

Related U.S. Application Data

(60) Provisional application No. 62/431,988, filed on Dec. 9, 2016.

(51) Int. Cl.
| | | |
|---|---|---|
| *A61K 35/35* | (2015.01) | |
| *A61L 27/36* | (2006.01) | |
| *A61K 38/18* | (2006.01) | |
| *A61L 27/48* | (2006.01) | |
| *A61L 27/54* | (2006.01) | |
| *A61L 27/56* | (2006.01) | |
| *A61K 48/00* | (2006.01) | |
| *A61K 51/04* | (2006.01) | |
| *A61P 17/02* | (2006.01) | |

(52) U.S. Cl.
CPC ...... *A61L 27/3629* (2013.01); *A61K 38/1866* (2013.01); *A61K 48/005* (2013.01); *A61K 48/0025* (2013.01); *A61K 51/0491* (2013.01); *A61L 27/3683* (2013.01); *A61L 27/48* (2013.01); *A61L 27/54* (2013.01); *A61L 27/56* (2013.01); *A61L 2300/414* (2013.01); *A61L 2300/64* (2013.01); *A61L 2430/34* (2013.01); *A61L 2430/40* (2013.01); *A61P 17/02* (2018.01)

(58) Field of Classification Search
CPC ............................... A61K 35/35; A61K 35/38
See application file for complete search history.

(56) References Cited

U.S. PATENT DOCUMENTS

| | | |
|---|---|---|
| 7,534,448 B2 | 5/2009 | Saitzman et al. |
| 7,928,280 B2 | 4/2011 | Hariri et al. |
| 8,894,707 B2 | 11/2014 | Zhao et al. |
| 2009/0035257 A1 | 2/2009 | Moseley et al. |
| 2009/0142836 A1 | 6/2009 | Wang et al. |
| 2012/0276039 A1 | 11/2012 | Courage et al. |
| 2013/0196915 A1 | 8/2013 | Wang et al. |
| 2014/0038301 A1 | 2/2014 | Ju et al. |
| 2014/0335046 A1 | 11/2014 | Matheny |
| 2016/0296635 A1* | 10/2016 | Wang .................. A61K 47/549 |
| 2017/0021058 A1* | 1/2017 | Huang ................ A61L 27/3645 |
| 2017/0354755 A1* | 12/2017 | Weinberger ............. A61L 27/52 |

OTHER PUBLICATIONS

Chen, N. et al., Cell adhesion on an artificial extracellular matrix using aptamer-functionalized PEG hydrogels, Biomaterials, 33: 1353-1362, 2012.
Battig, M. et al. Aptamer-functionalized superporous hydrogels for sequestration and release of growth factors regulated via molecular recognition, Biomaterials, 35(27): 8040-48, Sep. 2014 (Abstract).
Crapo, P. et al. An overview of tissue and whole organ decellularization processes, Biomaterials, 32(12): 3233-43, Apr. 2011.
Fan, T. et al., An aptamer-functionalized hydrogel for controlled protein release: A modeling study, Soft Matter, 7: 9326-34, 2011 (Abstract).
Reing, J. et al., The Effects of Processing Methods Upon Mechanical and Biologic Properties of Porcine Dermal Extracellular Matrix Scaffolds, Biomaterials, 31(33): 8626-33, Nov. 2010.
Soontornworajit, B. et al., Aptamer-functionalized in situ injectable hydrogel for controlled protein release, Biomacromolecules, 11(10): 2724-30, 2010 (Abstract).
Su, Z. et al., Enhancement of skin wound healing with decellularized scaffolds loaded with hyaluronic acid and epidermal growth factor, Mater Sci Eng C Mater Biol Appl, 44: 440-8, Nov. 2014 (Abstract).
Lahkin, A. et al., Aptamers: Problems, Solutions and Prospects, Acta Naturae, 5(4) ( 19): 34-43, 2013.
International Search Report and Written Opinion for PCT/US2017/065549, dated Mar. 29, 2018.

\* cited by examiner

*Primary Examiner* — Karen Cochrane Carlson
(74) *Attorney, Agent, or Firm* — Julie K. Staple; Dinsmore & Shohl LLP

(57) ABSTRACT

Methods and compositions for tissue regeneration of the present invention include a biocompatible porous composite of a decellularized tissue and an aptamer-functionalized hydrogel, wherein the aptamers of the aptamer-functionalized hydrogel specifically and reversibly bind to an active agent.

19 Claims, 10 Drawing Sheets
Specification includes a Sequence Listing.

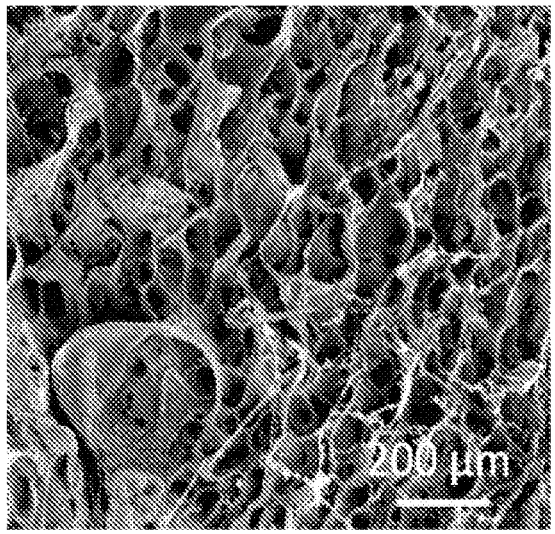
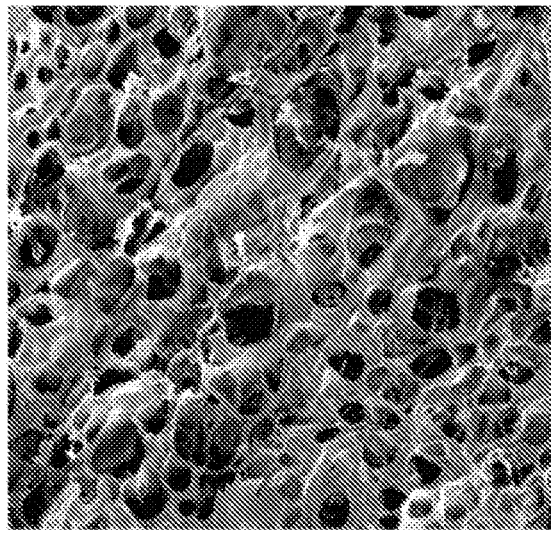
No hydrogel loading
FIG. 2A
25% hydrogel loading
FIG. 2B
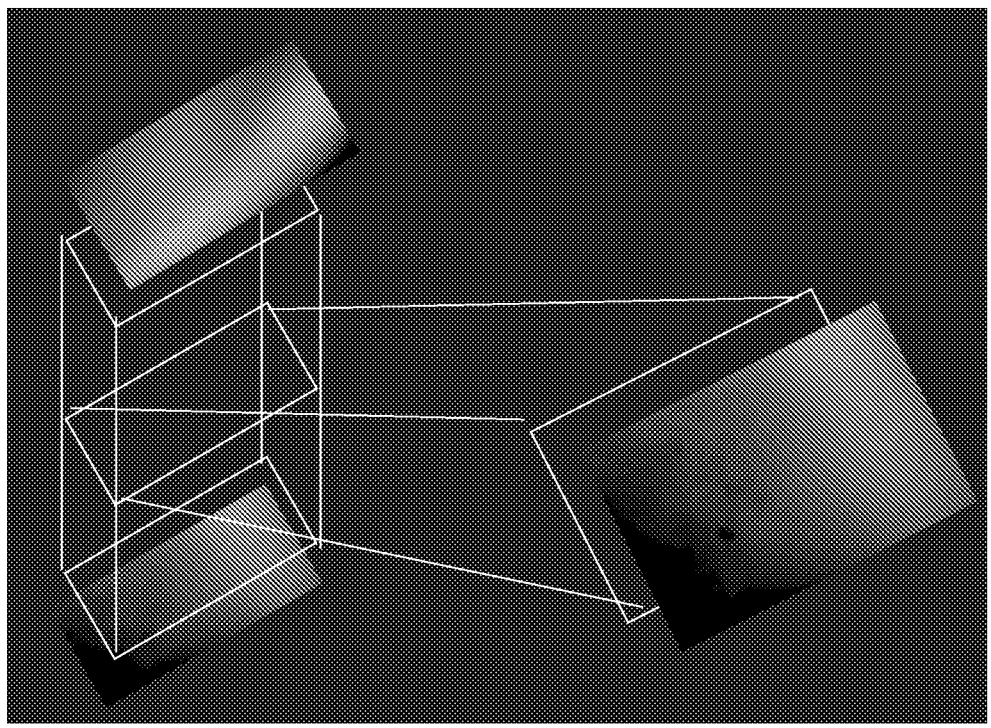
FIG. 2C

SEQUENCE LISTING

<160> NUMBER OF SEQ ID NOS: 1

<210> SEQ ID NO 1
<211> LENGTH: 36
<212> TYPE: DNA
<213> ORGANISM: Artificial Sequence
<220> FEATURE:
<223> OTHER INFORMATION: Anti-VEGF DNA aptamer

<400> SEQUENCE: 1
aaaaaaaaaa cccgtcttcc agacaagagt gcaggg     36

SEMI-SYNTHETIC TISSUE CONSTRUCTS FOR TISSUE REGENERATION

REFERENCE TO RELATED APPLICATION

This application claims priority from U.S. Provisional Patent Application Ser. No. 62/431,988, filed Dec. 9, 2016, the entire content of which is incorporated herein by reference.

GOVERNMENT SUPPORT

This invention was made with government support under Grant No. DMR1332351 awarded by the National Science Foundation. The Government has certain rights in the invention.

FIELD OF THE INVENTION

Generally described herein are methods and compositions relating to tissue regeneration. According to specific aspects, methods and compositions for tissue regeneration of the present invention include a biocompatible porous composite of a decellularized tissue and an aptamer-functionalized hydrogel.

BACKGROUND OF THE INVENTION

Tissue regeneration is a complex process implicated in healing from damage in the context of a variety of diseases or disorders such as skin damage from skin diseases, accidents, burns, and wounds, including surgical wounds. There is a continuing need tissue regeneration compositions and their methods of use.

SUMMARY OF THE INVENTION

Tissue regeneration compositions are provided according to aspects of the present invention which include a biocompatible porous composite of a decellularized tissue and an aptamer-functionalized hydrogel, wherein the aptamers of the aptamer-functionalized hydrogel specifically and reversibly bind to an active agent.

Tissue regeneration compositions are provided according to aspects of the present invention which include a biocompatible porous composite of a decellularized tissue and an aptamer-functionalized hydrogel, wherein the aptamers of the aptamer-functionalized hydrogel specifically and reversibly bind to an active agent, and wherein the active agent is reversibly bound to the aptamers.

Optionally, the decellularized tissue is loaded to less than 100% capacity with the aptamer-functionalized hydrogel, such as between 10% and 75% capacity with the aptamer-functionalized hydrogel, such as between 20% and 50% capacity with the aptamer-functionalized hydrogel.

In a preferred option, the decellularized tissue is a decellularized mammalian tissue.

The aptamer-functionalized hydrogel is optionally an aptamer-functionalized biological polymer.

An adjunct therapeutic agent and/or stem cell is optionally included in a tissue regeneration composition according to aspects of the present invention.

Optionally, a support is present in contact with the biocompatible porous composite.

An aptamer-functionalized hydrogel according to aspects of the present invention includes more than one type of aptamer, wherein each type of aptamer specifically and reversibly binds to a different active agent.

Methods of aiding tissue regeneration in a subject in need thereof are provided according to aspects of the present invention which include administering a tissue regeneration composition to the subject, wherein the tissue regeneration composition includes a biocompatible porous composite of a decellularized tissue and an aptamer-functionalized hydrogel, wherein the aptamers of the aptamer-functionalized hydrogel specifically and reversibly bind to an active agent, and wherein the active agent is reversibly bound to the aptamers.

Methods of aiding tissue regeneration in a subject in need thereof are provided according to aspects of the present invention wherein the subject has a wound, which include contacting the wound with the tissue regeneration composition, wherein the tissue regeneration composition includes a biocompatible porous composite of a decellularized tissue and an aptamer-functionalized hydrogel, wherein the aptamers of the aptamer-functionalized hydrogel specifically and reversibly bind to an active agent, and wherein the active agent is reversibly bound to the aptamers.

Optionally, the tissue is skin, an internal tissue or a tissue of an internal organ.

Methods of producing the tissue regeneration composition are provided according to aspects of the present invention which include loading a decellularized tissue with a precursor solution, the precursor solution comprising at least one aptamer-functionalized component; and polymerizing the precursor solution in situ in the decellularized tissue, thereby producing the tissue regeneration composition include a biocompatible porous composite of a decellularized tissue and an aptamer-functionalized hydrogel, wherein the aptamers of the aptamer-functionalized hydrogel specifically and reversibly bind to an active agent.

BRIEF DESCRIPTION OF THE DRAWINGS

FIG. 2A is an SEM image of porcine small intestine without aptamer-functionalized hydrogel;

FIG. 2B is an SEM image of porcine small intestine with aptamer functionalized hydrogel;

FIG. 2C is a schematic diagram illustrating that, after loading aptamer-functionalized hydrogel mixed with fluorescein (FAM), the top, middle, and bottom layers of decellularized intestine were examined by fluorescence microscopy;

DETAILED DESCRIPTION OF THE INVENTION

Figure 1A:
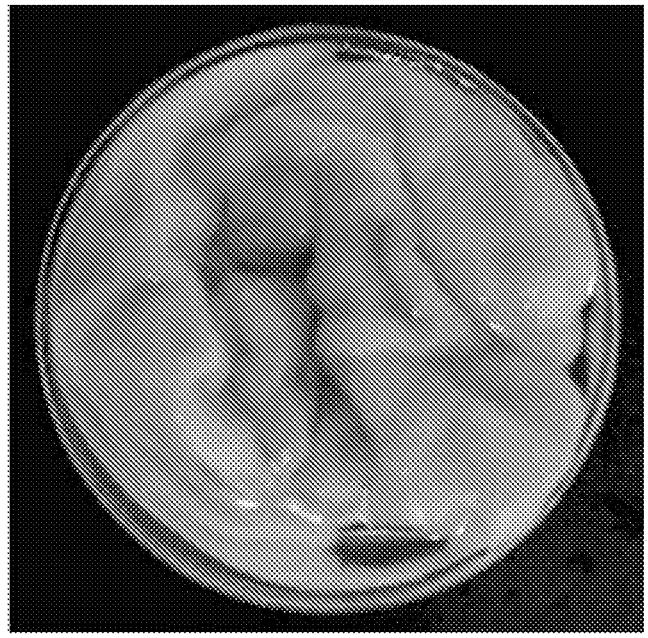
FIG. 1A is an image of porcine small intestine before decellularization.

Scientific and technical terms used herein are intended to have the meanings commonly understood by those of ordinary skill in the art. Such terms are found defined and used in context in various standard references illustratively including S. Klussman, Ed., The Aptamer Handbook: Functional Oligonucleotides and Their Applications, Wiley, 2006; J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W. H. Freeman & Company, 2004; Remington: The Science and Practice of Pharmacy, Lippincott Williams & Wilkins, 21st Ed., 2005; L. V. Allen, Jr. et al., Ansel's Pharmaceutical Dosage Forms and Drug Delivery Systems, 8th Ed., Philadelphia, Pa.: Lippincott, Williams & Wilkins, 2004; and L. Brunton et al., Goodman & Gilman's The Pharmacological Basis of Therapeutics, McGraw-Hill Professional, 12th Ed., 2011.

The singular terms "a," "an," and "the" are not intended to be limiting and include plural referents unless explicitly stated otherwise or the context clearly indicates otherwise.

Tissue regeneration compositions are provided according to aspects of the present invention which include a biocompatible porous composite of a decellularized tissue and an aptamer-functionalized hydrogel, wherein the aptamer binds specifically to an active agent.

The term "composite" as used herein refers to a combination in which the components are present together and where the individual components may or may not be physically different in combination compared to separately.

A decellularized tissue included in tissue regeneration compositions according to aspects of the present invention is an animal tissue processed to destroy intact cells and remove cytoplasm and cell membranes while leaving the extracellular matrix structure of the tissue substantially intact. Virtually any animal tissue characterized by an extracellular matrix structure can be processed to produce a decellularized tissue for inclusion in tissue regeneration compositions according to aspects of the present invention. According to aspects of tissue regeneration compositions of the present invention the decellularized tissue is derived from a tissue of a mammal, including, but not limited to, a human, a non-human primate, a pig, a cow, a horse, a rat, a mouse, a guinea pig, a rabbit, a goat, a cat or a dog.

The decellularized tissue is derived from any tissue or organ including, but not limited to, dermis, esophagus, heart, small intestine, large intestine, liver, spleen, stomach and urinary bladder.

The decellularized tissue all, or some, or only one of the tissue layers which ordinarily make up the tissue. One or more tissue layers can be removed to produce a decellarized tissue having a subset of the tissue layers that ordinarily make up the tissue.

For example, small intestine ordinarily has four cellular tissue layers when intact and four decellularized tissue layers when decellularized, the serosa, muscularis, submucosa and mucosa layers. According to particular embodiments, the submucosa tissue layer of small intestine (SIS) is isolated and used as a decellularized tissue incorporated into a biocompatible porous composite according to aspects of the present invention.

Methods of separating layers of tissues are well-known, including manual (physical) separation. Chemical or enzymatic agents can be used to loosen or destroy bonds between tissue layers.

A decellularized tissue is porous due to removal of cells, leaving a porous extracellular matrix structure.

Processes for producing a decellularized tissue generally include destruction of cells, such as by physical, chemical or enzymatic treatment such as treatment with a detergent, acid, enzyme or other cell lysing agent, and removal of the cells, nucleus and cytoplasmic contents, typically by washing, under conditions compatible with maintaining the integrity of the extracellular matrix of the tissue. Details of processes for producing decellularized tissues are included herein and in Crapo et al., An overview of tissue and whole organ decellularization processes, Biomaterials, 2011, 32:3233-43.

A hydrogel included in tissue regeneration compositions according to aspects of the present invention is a biocompatible polymer.

The term "biocompatible" refers to a polymer that is non-toxic and therefore compatible with administration to a subject without undue or excessive undesirable side effects.

The term "hydrogel" refers to a three-dimensional polymer network of hydrophilic polymers or polymers containing hydrophilic co-polymers, wherein the polymer network is insoluble in water and wherein water fills the space between the polymer chains. The polymer network may be formed by chemical crosslinking by covalent bonding or physical interactions such as ionic interactions, hydrogen bonds or hydrophobic interactions such as physical entanglement.

Hydrogels can be prepared with biocompatible synthetic materials to achieve specific properties at the micro- or nano-scale level. The manipulation of the molecular weight or molecular weight distribution can be used to modulate the mechanical strength of hydrogels to satisfy different requirements. Hydrogels can be designed to modulate the porosity of the network, which can be advantageously used to control the release rate in conjunction with affinity of nucleic acid aptamers.

Hydrogels can be formed from a wide variety of biocompatible polymeric materials, including, but not limited to, polyurethane, silicone, copolymers of silicone and polyurethane, polyolefins such as polyisobutylene and polyisoprene, nitrile, neoprene, collagen, alginate and the like. For example, suitable hydrogels can be formed from polyvinyl alcohol, acrylamides such as polyacrylic acid and poly(acrylonitrile-acrylic acid), polyurethanes, polyethylene glycol, polyethylene glycol diacrylate (PEGDA), poly(N-vinyl-2-pyrrolidone), acrylates such as poly(-hydroxy ethyl methacrylate) and copolymers of acrylates with N-vinyl pyrrolidone, N-vinyl lactams, a poly(lactide-co-glycolide), acrylamide, polyurethanes, polyacrylonitrile, poloxamer, N-isopropylacrylamide copolymers, poly(N-isopropylacrylamide), poly(vinyl methyl ether), poly(NIPAAm-co-PEG) and the like.

Suitable hydrogels can be formed from ABA triblock containing hydrophobic polyester (A-block) and hydrophilic polyether; triblock copolymer of poly(D,L-lactide-block-ethylene oxide-block-D,L-lactide) PLA-PEO-PLA, triblock copolymer of poly(L-lactide-block-ethylene oxide-block-L-lactide) PLLA-PEO-PLLA, triblock copolymer of poly[(D,L-lactide-coglycolide)-block-ethylene oxide-block-(D,L-lactide-co-glycolide)] PLGA-PEO-PLGA, triblock copolymer of poly[(L-lactide-coglycolide)-block-ethylene oxide-block-(L-lactide-co-glycolide)] PLLGA-PEO-PPLGA, triblock copolymer of poly[(D,L-lactide-coglycolide)-block-ethylene oxide-block-(D,L-lactide-co-glycolide)] PLGA-PEO-PLGA, triblock copolymer of poly(.epsilon.-caprolactone-block-ethylene oxide-block-ε-caprolactone) PCL-PEO-PCL, triblock copolymer of poly[(D,L-lactide-co-ε-caprolactone)-block-ethylene oxide-block-(D,L-lactide-co-ε-caprolactone)] PLC-PEO-PLC.

Hydrogels can be prepared to include, or consist of, natural biomolecules. Naturally derived polymer hydrogels functionalized with one or more aptamers and included in a tissue regeneration composition according to aspects of the present invention include polysaccharides, such as, but not limited to cellulose, chitin, chitosan, hyaluronic acid (HA), chondroitin, dextran, alginate and pectin, as well as derivatives thereof. Naturally derived polymer hydrogels functionalized with one or more aptamers and included in a tissue regeneration composition according to aspects of the present invention include proteins, such as, but not limited to, fibrin, collagen, gelatin, heparin, fibronectin, laminin, elastin, and fibrinogen, as well as derivatives thereof. The term "derivative" when used with reference to a naturally-derived polymer derivative refers to a modified but structurally related polymer that retains the function of the reference naturally-derived polymer or has improved function.

The decellularized tissue is loaded with the aptamer-functionalized hydrogel to produce a biocompatible porous composite. Loading of the decellularized tissue is achieved by contacting the decellularized tissue with the aptamer-functionalized hydrogel. In a preferred aspect of the present invention, loading of the decellularized tissue is achieved by contacting the decellularized tissue with a precursor solution including one or more aptamer-functionalized hydrogel precursors, wherein the precursor solution is then reacted and/or incubated under hydrogel formation conditions to form an aptamer-functionalized hydrogel in situ in a decellularized tissue.

A precursor solution forms a hydrogel in the decellularized tissue via various chemical or physical crosslinking methods such as free radical polymerization, click chemistry, Michael addition, di-sulfide crosslinking, Schiff base crosslinking, ionic crosslinking, hybridization-mediated crosslinking, enzyme-mediated crosslinking, electrostatic interactions, redox reactions, stimuli-responsive solubility change or phase transitions, and self-assembly mediated by complementary binding or host-guest interactions, depending on the identity of the components included in the precursor solution.

According to preferred aspects of the present invention, the decellularized tissue is loaded with the aptamer-functionalized hydrogel to less than 100% capacity of the decellularized tissue. Capacity of the decellularized tissue is calculated by calculation of a swelling volume ratio. For example, the decellularized tissue is freeze dried and weighed to determine the "dry weight." The decellularized tissue is immersed in phosphate buffered saline to hydrate and swell the decellularized tissue and the hydrated swollen decellularized tissue is weighed to determine the "swollen weight." Calculation of the swollen weight—dry weight/dry weight determines the swelling volume ratio.

According to preferred aspects of the present invention, the decellularized tissue is loaded with the aptamer-functionalized hydrogel to between 10% and 75% capacity with the aptamer-functionalized hydrogel.

According to preferred aspects of the present invention, the decellularized tissue is loaded with the aptamer-functionalized hydrogel to between 20% and 50% capacity with the aptamer-functionalized hydrogel.

Optionally, a biocompatible porous composite of a decellularized tissue and an aptamer-functionalized hydrogel includes at least two layers, a layer of decellularized tissue and a layer of aptamer-functionalized hydrogel.

In a further option, a biocompatible porous composite includes at least three layers, a layer of decellularized tissue disposed between two layers of aptamer-functionalized hydrogel. In such a "sandwich" layer configuration, the aptamer-functionalized hydrogel (with or without the active agent reversibly bound to the aptamer-functionalized hydrogel) penetrates into the pores of the layer of decellularized tissue from both sides of the decellularized tissue.

A two layer configuration can be assembled, for example, by placing the hydrogel, such as aptamer-functionalized hydrogel or aptamer-functionalized hydrogel precursor, in contact with one side of a two sided, such as a substantially planar, decellularized tissue. A "sandwich" layer configuration can be assembled, for example, by contacting both sides of a two sided, such as a substantially planar, decellularized tissue, with a hydrogel, such as aptamer-functionalized hydrogel or aptamer-functionalized hydrogel precursor.

According to one example, a "sandwich" layer configuration can be assembled, for example, by making holes extending through a two sided, such as a substantially planar, decellularized tissue, and then contacting at least one side of the decellularized tissue with a hydrogel, such as aptamer-functionalized hydrogel or aptamer-functionalized hydrogel precursor, whereby the aptamer-functionalized hydrogel or aptamer-functionalized hydrogel precursor flows from one side of the decellularized tissue to the other through the holes.

According to still further options, additional layers of decellularized tissue and/or aptamer-functionalized hydrogel may be incorporated in a biocompatible porous composite according to aspects of the present invention.

According to aspects of the present invention, two or at least two layers of a biocompatible porous composite are chemically bonded to promote stability of the biocompatible porous composite.

Optionally, a composite having two or more layers of: 1) aptamer-functionalized hydrogel and 2) decellularized tissue is provided wherein at least two of the two or more layers are chemically bonded to each other either directly or indirectly. According to aspects of the present invention, the 1) aptamer-functionalized hydrogel and 2) decellularized tissue are directly bonded to each other.

Bonding between the 1) aptamer-functionalized hydrogel and 2) decellularized tissue can be achieved by various methods such as by bonding between functional groups present on the 1) aptamer-functionalized hydrogel and 2) decellularized tissue. Optionally, the 1) aptamer-functionalized hydrogel and/or 2) decellularized tissue can be modified to introduce functional groups for reaction to create bonds between the 1) aptamer-functionalized hydrogel and 2) decellularized tissue.

Reactive functional groups include alkyne, hydrazide, succinylate, disulfide, acrydite, thiol, carboxyl, amine, amino, carboxylate, halide, ester, alcohol, carbamide, aldehyde, chloromethyl, sulfur oxide, nitrogen oxide, epoxy and/or tosyl functional groups.

For example, a cross-linking agent can be used to create bonds, via reacting the reactive functional groups, between the 1) aptamer-functionalized hydrogel and 2) decellularized tissue. Such cross-linking agents include, for example, glutaraldehyde, NHS esters, and imidoesters. According to particular aspects, the crosslinking agent is a naturally occurring crosslinker, such as genipin.

Alternatively, or in addition, a linker can be used to create bonds between the 1) aptamer-functionalized hydrogel and 2) decellularized tissue. Such a linker can be any molecule or structure which is bound to both the 1) aptamer-functionalized hydrogel and 2) decellularized tissue and which does not interfere with the function of either. A linker can be, without limitation, a chain of atoms, a peptide, a nucleic acid, a carbohydrate, a chemical compound, and/or a macromolecular structure.

A biocompatible porous composite according to aspects of the present invention is generally planar and may be configured to have any of a variety of shapes such as rectangular, circular, ovoid, or any regular or irregular shape convenient to place in contact with a region of a body to aid tissue regeneration and/or place in contact with a wound for treatment of the wound.

A biocompatible porous composite according to aspects of the present invention contains multiple layers to achieve a generally non-planar composite and may be configured to have any of a variety of shapes such as rectangular, circular, ovoid, or any regular or irregular shape convenient to place in contact with a region of a body to aid tissue regeneration and/or place in contact with a wound for treatment of the wound.

The term "aptamer" refers to a peptide and/or nucleic acid that specifically and reversibly binds to a specified active agent. According to aspects of the present invention, an included aptamer is a DNA aptamer, an RNA aptamer, an L-oligonucleotide (Spiegelmer) aptamer, an aptamer with chemical modifications, or including a combination of two or more thereof.

An aptamer included in a tissue regeneration composition optionally includes one or more modified DNA, RNA and/or L-oligonucleotides to enhance stability or affinity of the aptamer.

An aptamer is selected or designed to bind specifically and reversibly to a specified active agent to provide a therapeutic activity of the active agent on a tissue to be treated so as to aid in tissue regeneration. An active agent is any substance capable of providing a beneficial effect to aid in tissue regeneration including, but not limited to, a small molecule drug, a peptide or a protein.

An active agent is any substance capable of providing a beneficial effect to aid in tissue regeneration including, but not limited to, bone morphogenetic proteins (BMPs), brain-derived neurotrophic factor (BDNF), ciliary neurotrophic factor (CNTF), epidermal growth factor (EGF), erythropoietin (EPO), fibroblast growth factor (FGF), glial cell line-derived neurotrophic factor (GDNF), granulocyte-macrophage colony-stimulating factor (GM-CSF), granulocyte macrophage colony-stimulating factor (GM-CSF), growth differentiation factor-9 (GDF9), hepatocyte growth factor (HGF), hepatoma-derived growth factor (HDGF), insulin-like growth factor (IGF), keratinocyte growth factor (KGF), migration-stimulating factor (MSF), myostatin (GDF-8), neurotrophins such as nerve growth factor (NGF), neurotrophin 3, neurotrophin 4, neurotrophin 5, platelet-derived growth factor (PDGF), thrombopoietin (TPO), T-cell growth factor (TCGF), transforming growth factor alpha (TGF-α), transforming growth factor beta (TGF-β), tumor necrosis factor-alpha (TNF-α), vascular endothelial growth factor (VEGF), placental growth factor (PGF) and interleukins such as IL-1, IL-2, IL-3, IL-4, IL-5, IL-6 and IL-7.

An aptamer-functionalized hydrogel optionally includes more than one type of aptamer, wherein each type of aptamer specifically and reversibly binds to a different active agent. Thus, combinations of two or more active agents are incorporated into a tissue regeneration composition by binding to two more types of aptamers, wherein each type of aptamer specifically binds to one of the two or more active agents, and used in methods according to aspects of the present invention. According to aspects of the present invention, VEGF incorporated into a tissue regeneration composition by binding to an aptamer that specifically binds to VEGF (VEGF-specific aptamers) and PDGF is incorporated into a tissue regeneration composition by binding to an aptamer that specifically binds to PDGF (PDGF-specific aptamers). Any combination of two or more active agents selected from the group consisting of: bone morphogenetic proteins (BMPs), brain-derived neurotrophic factor (BDNF), ciliary neurotrophic factor (CNTF), epidermal growth factor (EGF), erythropoietin (EPO), fibroblast growth factor (FGF), glial cell line-derived neurotrophic factor (GDNF), granulocyte-macrophage colony-stimulating factor (GM-CSF), granulocyte macrophage colony-stimulating factor (GM-CSF), growth differentiation factor-9 (GDF9), hepatocyte growth factor (HGF), hepatoma-derived growth factor (HDGF), insulin-like growth factor (IGF), keratinocyte growth factor (KGF), migration-stimulating factor (MSF), myostatin (GDF-8), neurotrophins such as nerve growth factor (NGF), neurotrophin 3, neurotrophin 4, neurotrophin 5, platelet-derived growth factor (PDGF), thrombopoietin (TPO), T-cell growth factor (TCGF), transforming growth factor alpha (TGF-α), transforming growth factor beta (TGF-β), tumor necrosis factor-alpha (TNF-α), vascular endothelial growth factor (VEGF), placental growth factor (PGF) and interleukins such as IL-1, IL-2, IL-3, IL-4, IL-5, IL-6 and IL-7 is specifically contemplated for inclusion in compositions and methods according to aspects of the present invention.

In the case of a nucleic acid aptamer, the aptamer is characterized by specific and reversible binding a specified active agent wherein the binding is not Watson/Crick base pairing or triple helix binding with a second and/or third nucleic acid. Such binding may include Van der Waals interaction, hydrophobic interaction, hydrogen bonding and/or electrostatic interactions, for example.

Peptide-based aptamers are characterized by specific and reversible binding to a specified active agent wherein the aptamer is not a naturally occurring binding partner for the specified active agent.

Peptide and nucleic acid aptamers can be modified to add one or more functional groups such as acrydite, biotin, thiol, amino and the like. Such functional groups can be disposed at the 5' and/or 3' end of nucleic acid aptamers or at the N-terminus and/or C-terminus of peptide aptamers.

According to particular aspects of the present invention, an aptamer included in compositions and methods of the present invention is a nucleic acid aptamer. Nucleic acid aptamers can be single-stranded DNA, double-stranded DNA, RNA, or modified DNA or RNA. In one aspect, nucleic acid aptamers included in compositions and methods of the present invention are single-stranded nucleic acids that are identified and isolated from DNA/RNA libraries.

Nucleic acid aptamers included in compositions and methods of the present invention are characterized by tunable stability in biological environments and their biodegradability can be controlled by the degree of nucleotide modification.

Nucleic acid aptamers included in compositions and methods of the present invention have increased tolerance to harsh thermal, physical, and chemical conditions and exert little or no immunogenicity or toxicity.

Techniques for identification and generation of peptide and nucleic acid aptamers and their use are known in the art as described, for example, in F. M. Ausubel et al., Eds., Short Protocols in Molecular Biology, Current Protocols, Wiley, 2002; S. Klussman, Ed., The Aptamer Handbook: Functional Oligonucleotides and Their Applications, Wiley, 2006; and J. Sambrook and D. W. Russell, Molecular Cloning: A Laboratory Manual, Cold Spring Harbor Laboratory Press, 3rd Ed., 2001. Technologies for functionalized aptamer screening methods, such as Systematic Evolution of Ligands by Exponential Enrichment (SELEX), are well known in the art and can be used to select one or more nucleic acid aptamers to be included in compositions and methods of the present invention.

A hydrogel is functionalized with aptamers by either directly or indirectly binding the aptamers to the hydrogel. According to aspects of the present invention, the hydrogel is functionalized with nucleic acid aptamers by directly binding the nucleic acid aptamers to the hydrogel.

The aptamers may be bound to a specified active agent before or after binding of the aptamers to the hydrogel.

Optionally, the aptamer-functionalized hydrogel includes more than one type of aptamer, wherein each type of aptamer specifically and reversibly binds to a different active agent.

According to aspects of the present invention, nucleic acid aptamers modified to include a reactive functional group at the 5' or 3' end are chemically reacted with a hydrogel-forming component, such as a monomer or polymer, forming an aptamer-modified hydrogel-forming component. The aptamer-modified hydrogel-forming component is then reacted with one or more other hydrogel-forming components are provided as a precursor solution which is reacted or incubated under hydrogel formation conditions to form an aptamer-functionalized hydrogel. In a preferred aspect of the present invention, the precursor solution is or incubated under hydrogel formation conditions to form an aptamer-functionalized hydrogel in situ in a decellularized tissue.

Reactive functional groups include alkyne, hydrazide, succinylate, disulfide, acrydite, thiol, carboxyl, amine, amino, carboxylate, halide, ester, alcohol, carbamide, aldehyde, chloromethyl, sulfur oxide, nitrogen oxide, epoxy and/or tosyl functional groups.

For example, an acrydite-functionalized aptamer is bound to a hydrogel-forming polymer or monomer, for example, an acrylamide monomer. Aptamer-modified acylamide is mixed with bis-acrylamide forming a precursor solution. When ready to contact a decellularized tissue, ammonium persulfate (APS) and N,N,N',N'-tetramethylenediamine (TEMED) are added to the precursor solution to initiate free radical polymerization and formation of the aptamer-functionalized hydrogel occurs during the decellularized tissue loading, producing an aptamer-functionalized hydrogel in-situ in the decellularized tissue. The active agent can be bound to the aptamers before or after production of the aptamer-functionalized hydrogel.

In a further example, a gel-forming polymer, such as alginate, can be activated with N-hydroxysuccinimide (NHS). The activated alginate is reacted with nucleic acid aptamers bearing primary amino groups to form an aptamer-alginate conjugate. The conjugate is then reacted with ions (e.g., calcium ion) to form an alginate hydrogel. The active agent can be bound to the aptamers before or after production of the aptamer-functionalized hydrogel.

Click chemistry may be used to functionalize a hydrogel with aptamers. Click chemistry is based on the reaction between an azide and an alkyne. For instance, hyaluronan can be functionalized with 11-azido-3,6,9-trioxaundecan-1-amine to produce hyaluronan with azide groups attached to its side chains. Aptamers functionalized with an alkyne group that at either 5' or 3' end can be reacted with the azide-functionalized hyaluronan to produce aptamer-functionalized hyaluronan. A decellularized tissue is loaded with the aptamer-functionalized hyaluronan hydrogel precursor above the sol-gel transition temperature and allowed to cool to form the aptamer-functionalized hydrogel in situ in the decellularized tissue. The active agent can be bound to the aptamers before or after production of the aptamer-functionalized hydrogel.

In a further example, primary amino groups of gelatin are functionalized with N-((β-maleimidopropyloxy)succinimide ester (BMPS) to produce maleimide groups. The maleimide groups of the functionalized gelatin are then reacted with nucleic acid aptamers bearing thiol groups to produce aptamer-functionalized gelatin. A decellularized tissue is loaded with the aptamer-functionalized gelatin in the presence of glutaraldehyde to crosslink the aptamer-functionalized gelatin and form an aptamer-functionalized hydrogel in situ in the decellularized tissue. The active agent can be bound to the aptamers before or after production of the aptamer-functionalized hydrogel.

In a further example, primary amino groups of collagen are functionalized with N-((β-maleimidopropyloxy)succinimide ester (BMPS) to produce maleimide groups. The maleimide groups of the functionalized collagen are then reacted with nucleic acid aptamers bearing thiol groups to produce aptamer-functionalized collagen. A decellularized tissue is loaded with the aptamer-functionalized collagen in the presence of glutaraldehyde to crosslink the aptamer-functionalized collagen and form an aptamer-functionalized hydrogel in situ in the decellularized tissue. The active agent can be bound to the aptamers before or after production of the aptamer-functionalized hydrogel.

Alternatively, or in addition, a hydrogel can be functionalized with nucleic acid aptamers by indirectly binding the nucleic acid aptamers to the hydrogel. For example, the aptamers can be bound to a linker and the linker is bound to the hydrogel. A linker can be any molecule or structure which is bound to both an aptamer and a hydrogel and which does not interfere with the function of the aptamer. A linker can be, without limitation, a chain of atoms, a peptide, a nucleic acid, a carbohydrate, a chemical compound, and/or a macromolecular structure. The active agent can be bound to the aptamers before or after binding of the aptamers with a linker and before or after binding of the linker to the hydrogel.

Release of the active agent reversibly bound to the aptamers can be adapted to provide for faster or slower release when in place as a tissue regeneration composition in a subject in need thereof. Release of the active agent reversibly bound to the aptamers can be adapted to provide for faster or slower release by varying one or more of: 1) the molar ratio of active agent to aptamers in the composite composition; 2) the binding affinity of the aptamers for the active agent; and 3) the concentration of the aptamers.

According to aspects of the present invention, a tissue regeneration composition includes a biocompatible porous composite of a decellularized tissue and an aptamer-functionalized hydrogel, wherein the aptamers of the aptamer-functionalized hydrogel specifically and reversibly bind to an active agent and wherein the aptamers are reversibly bound to the active agent. Amounts of active agent in the composition according to aspects of the present invention are in the range of about 0.4 micrograms per gram of the biocompatible porous composite to about 40 micrograms per gram of the biocompatible porous composite. Amounts of aptamers in the composition according to aspects of the present invention are in the range of about 0.1 nanomoles per gram of the biocompatible porous composite to about 10 nanomoles per gram of the biocompatible porous composite.

Methods of aiding tissue regeneration in a subject in need thereof include administering a tissue regeneration composition according to aspects of the present invention to one or more tissues of the subject.

The subject in need thereof has one or more diseases or undesirable conditions for which aiding in tissue regeneration treats the one or more diseases or undesirable conditions.

Any tissue of a subject can be contacted with a tissue regeneration composition according to aspects of the present invention to aid in treatment of a disease or undesirable condition affecting the tissue of the subject. The tissue contacted with a tissue regeneration composition is an internal tissue according to aspects of the present invention. The tissue contacted with a tissue regeneration composition is a tissue of an internal organ according to aspects of the present invention.

Administering a tissue regeneration composition according to aspects of the present invention to one or more tissues of the subject includes contacting the one or more tissues of the subject with the tissue regeneration composition. Thus, administering a tissue regeneration composition according to aspects of the present invention to one or more internal tissues of the subject includes a surgical step to contact an internal tissue or organ to treat the one or more diseases or undesirable conditions affecting the internal tissue or organ.

The tissue contacted with a tissue regeneration composition is skin according to aspects of the present invention.

Non-limiting examples of diseases or undesirable conditions treated using methods according to aspects of the present invention include venous ulcers, diabetic ulcers, heart disease, vascular damage or dysfunction, bladder wall damage or dysfunction, tendon damage or dysfunction, hernia, and wounds, including but not limited to full-thickness skin wounds.

The term "subject" as used herein refers to any animal subject, preferably a mammal, such as humans, non-human primates, cats, dogs, sheep, cows, goats, horses, pigs, poultry, birds, rabbits and rodents. Subjects can be either gender and can be any age.

The terms "treats," "treatment," "treating" and grammatical variants thereof as used herein refer to alleviating, inhibiting or ameliorating a disease or undesirable condition, symptoms or signs of a disease or undesirable condition, and preventing symptoms or signs of a disease or undesirable condition, and include, but are not limited to therapeutic, cosmetic and/or prophylactic treatments.

A tissue regeneration composition can be administered by itself or in conjunction with an adjunct therapeutic agent or support.

An adjunct therapeutic agent is a therapeutic agent in addition to the one or more active agents specifically bound to the aptamers included in the tissue regeneration composition. Examples of adjunct therapeutic agents that can be administered in conjunction with compositions and methods of the present invention include, but are not limited to, non-steroidal anti-inflammatory agents, anti-inflammatory agents, antibiotics, antivirals, antineoplastic agents, analgesics, antipyretics, antidepressants, antipsychotics, anticancer agents, anti-osteoporosis agents, anti-osteonecrosis agents, antihistamines, anxiolytics, chemotherapeutic agents, growth factors, hormones, vasoactive agents and combinations of two or more thereof.

According to particular aspects of the present invention, an antibiotic is an adjunct therapeutic agent included in a composition and/or administered to a subject.

Stem cells are optionally included in a composition according to the present invention. The type of stem cell included can vary depending on the condition to be treated and include, without limitation, embryonic stem cells, adult stem cells and induced pluripotent stem cells. Mesenchymal stem cells are included in compositions and administered to a subject according to aspects of the present invention.

A tissue regeneration composition optionally includes a support. An included support allows for handling and manipulating the tissue regeneration composition. An included support optionally remains in contact with the tissue regeneration composition when the tissue regeneration composition is in contact with a tissue. For example, an included support is a bandage or other type of wound dressing which at least partially covers the tissue regeneration composition when it is in place in contact with an external wound of a subject.

According to aspects of the present invention, a tissue regeneration composition and/or a biocompatible porous composite of a decellularized tissue and an aptamer-functionalized hydrogel is lyophilized, such as for storage or transport.

Embodiments of inventive compositions and methods are illustrated in the following examples. These examples are provided for illustrative purposes and are not considered limitations on the scope of inventive compositions and methods.

EXAMPLES

Decellularized Intestine (DI) Preparation

Clean the inner side remains with tap water (try to flush away all the visible attachments and soak it into water for around 10 min). Cut the small intestine (SI) into small pieces and remove all the fat tissues. Soak the samples in 3% TRITON X-100™ (2-[4-(2,4,4-trimethylpentan-2-yl)phenoxy]ethanol) overnight. Wash the samples with ddH$_2$O. Soak the samples in 3% SDS overnight in a 4° C. refrigerator. Wash the samples with ddH$_2$O. Soak the samples with 1% w/v penicillin diluted into ddH$_2$O overnight and freeze dry the samples. Store the materials in −20° C.

Figure 1B:
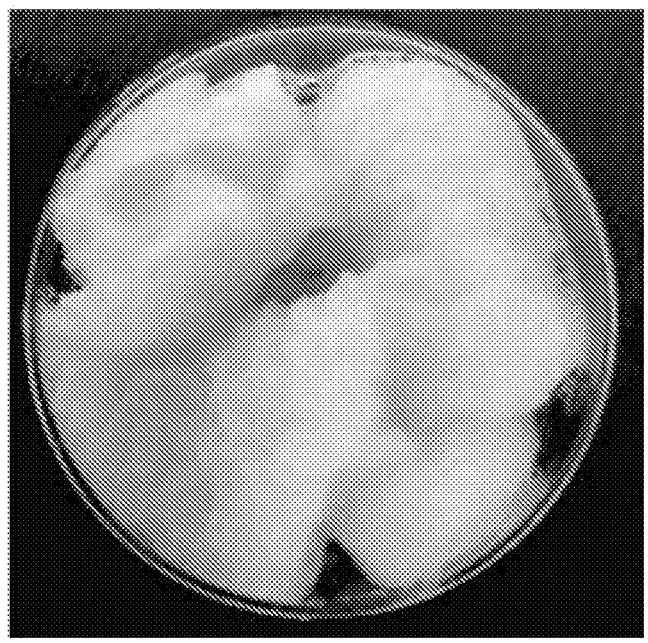
FIG. 1B is an image of porcine small intestine after decellularization.
Figure 1C:
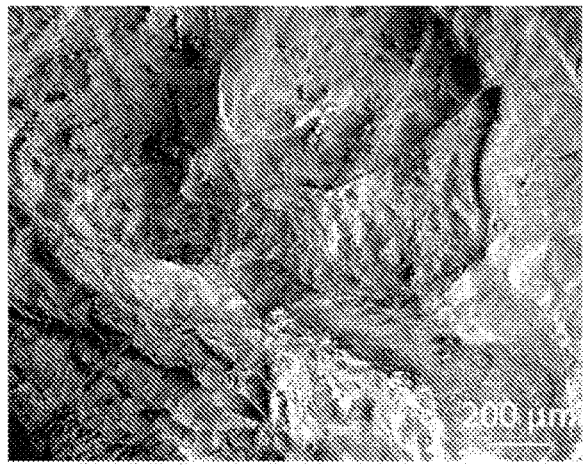
FIG. 1C is scanning electron micrograph (SEM) image of porcine small intestine before decellularization.
Figure 1D:
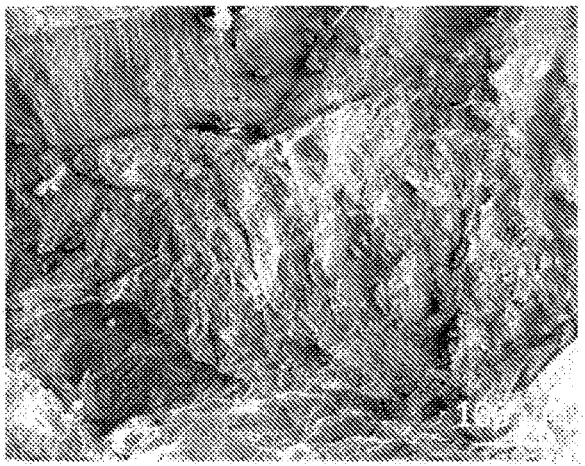
FIG. 1D is an SEM image of porcine small intestine before decellularization.
Figure 1E:
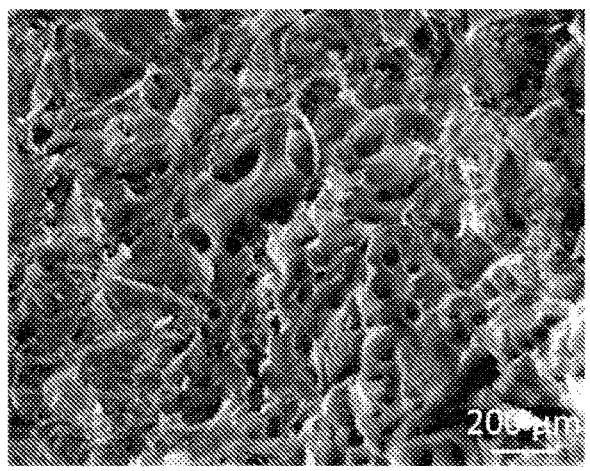
FIG. 1E is an SEM image of porcine small intestine after decellularization.
Figure 1F:
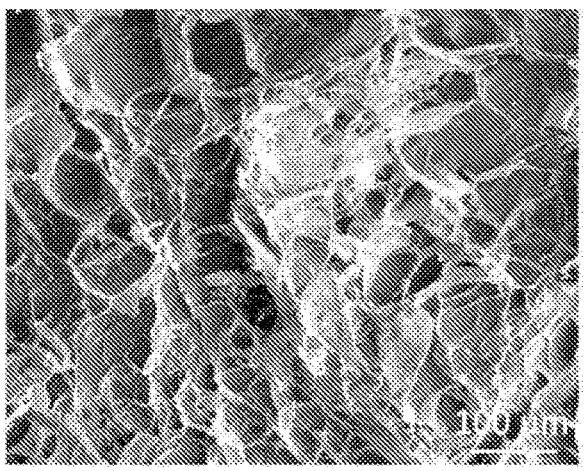
FIG. 1F is an SEM image of porcine small intestine after decellularization.

A comparison of porcine small intestine before and after decellularization is shown in FIGS. 1A and 1B, respectively. FIGS. 1C and 1D are scanning electron micrograph (SEM) images of porcine small intestine before decellularization. FIGS. 1E and 1F are SEM images of porcine small intestine after decellularization.

Gelatin-Methacrylate Preparation

Weigh (84 mg, depending on the molecular weight of that batch of material) NaHCO$_3$ and dissolve into 10 ml ddH$_2$O making 10 ml 0.1 M NaHCO$_3$. Gelatin (Porcine skin, 100 g bloom) was weighed and dissolved in NaHCO$_3$ solution. Add N-Hydroxysuccinimide ester (NHS)-MA DMSO solution into the gelatin solution. The Gelatin-MA solution is washed using a 10 kDa centrifugal filter. The solution is frozen at −20° C. and thawed at 37° C. upon use.

Aptamer Conjugation with Gelatin-Methacrylate

Reduced HS-DNA (Anti-VEGF DNA aptamer: /5ThioMC6-D/AAAAAAAAAAACCCGTCTTCCA-GACAAGAGTGCAGGG; SEQ ID NO: 1) was mixed with Gelatin-MA at 37° C. to prepare a 1 mL solution. Add 0.7 µl 0.05% DMPP solution to the mixture and incubate the solution at 37° C. for one hour. The mixture was washed and the product was collected using the centrifugal filter unit.

Loading Precursor Solution (Aptamer-Gelatin+PEGDA) into Decellularized Intestine (DI)

Mix the gelatin-aptamer solution with PEGDA. Load the mixture into the DI tissues to form the semi-synthetic tissue construct. Transfer the tissue samples to a 15 ml centrifuge tube for washing using ddH$_2$O. Freeze the materials in a −80° C. refrigerator for 2 hours and freeze dry the tissues for 24 hours in a petri dish. Keep the materials in a −20° C. freezer until use.

FIG. 2A is an SEM image of decellularized porcine small intestine before aptamer-functionalized hydrogel loading. FIG. 2B is an SEM image of decellularized porcine small intestine after aptamer-functionalized hydrogel loading.

FIG. 2C is a schematic diagram illustrating that, after loading aptamer-functionalized hydrogel mixed with fluorescein (FAM), the top, middle, and bottom layers of decellularized intestine were examined by fluorescence microscopy.

Vascular Endothelial Growth Factor (VEGF165) Loading

Put the DI-Gelatin-Aptamer semi-synthetic construct into a 10 ml centrifuge tube and spread the VEGF solution onto the surface of the construct. Allow the surface solution permeate to the construct before continuing the VEGF loading. Recap the centrifuge tubes and move them to a 4° C. refrigerator overnight.

In Vivo Application Example

Mice are the most widely used animal model for testing small size biomaterials (area smaller than 2 cm$^2$) in skin wound healing. Six mice are used for each experimental group. A wound size of ~5 mm in diameter is created in the dorsal skin. Wound healing is then observed over a period of 21 days.

The effect of the biomaterials of the present invention is evaluated using the following assessment modalities:

1. Imaging to measure the scar size with a camera.
2. Examination and measurement of cell infiltration and acute inflammation.
3. Histological analysis of the capillary vessel number and size in the new skin In this in vivo example: A sterile 8 mm biopsy punch is used to create two clean-cut, symmetrical, full-thickness excisional wounds on either side of the dorsal midline. The DI-Aptamer-VEGF hydrogel and control biomaterials are implanted on each side of the punch in the same mouse. Six mice are used. Wound size is imaged by a camera to calculate the macroscopic healing speed at day 0, 3, 7, 14, and 21. The wound healing speed is calculated by comparing with the wound size at day 0. Mice are sacrificed at predetermined time points (e.g., 7, 14 days or 21 days). The skin of the back is removed using surgical scissors and the wound site is isolated via a 10 mm biopsy punch. Half of the tissue is fixed in paraformaldehyde and half of the tissue is snap-frozen in liquid nitrogen and stored at −80° C. for further analysis. The samples are fixed using 4% paraformaldehyde, transferred to ethanol and embedded in a paraffin block. The blocks are then sectioned at 6 µm thickness by microtome followed by (H&E) staining. Normal cell and immune cell infiltration are counted from the microscopic images. Neutrophil cell infiltration is analyzed within 3 days. The capillary vessel size and number are calculated by microscopy analysis. Cadherin and alpha-actin are used to stain the sectioned tissue slices. Trichrome staining is used to stain collagen and other ECM if desired. Sectioned tissue slices are dehydrated and used for SEM imaging of decellularized tissue degradation and new ECM synthesized by host cells. Staining of proteins including CD31, Cytokeratin 10 (CK10) and cytokeratin 14 (CK14) is performed. Frozen materials are used for protein extraction and gene expression analysis if desired.

Tissue regeneration compositions described herein have good mechanical properties. For these experiments, the decellularized intestine (DI) or decellularized intestine with gelatin-aptamer hydrogel (DI+G) is cut into rectangular strips with dimensions of 5 mm×30 mm. After the decellularized intestine is fixed by clips, the thickness of the sample is measured using a digital caliper. During the test, the samples are pulled at a rate of 500 mm/min and elongated to a failure. Values are converted to stress-strain curves and the initial modulus is calculated from the initial gradient of the resulting curves (0-10% elongation). The Peak stress, Young's modulus, and strain at break are extrapolated from the stress-strain curves.

Figure 3A:
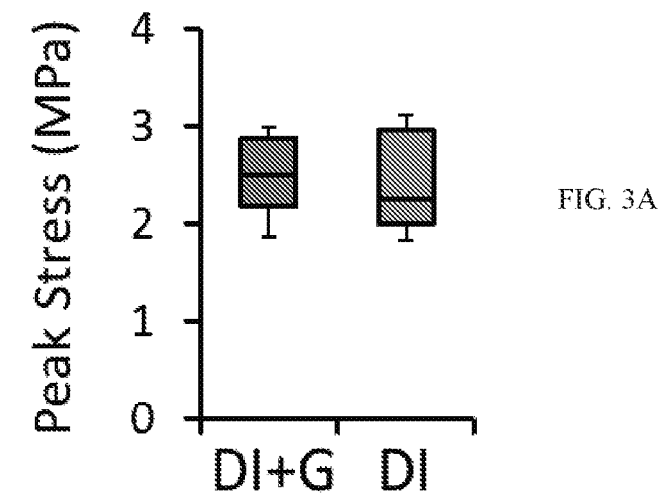
FIG. 3A is a graph showing results of mechanical property, peak stress, in decellularized intestine alone (DI) or in decellularized tissue loaded with aptamer-functionalized hydrogel (DI+G)
Figure 3B:
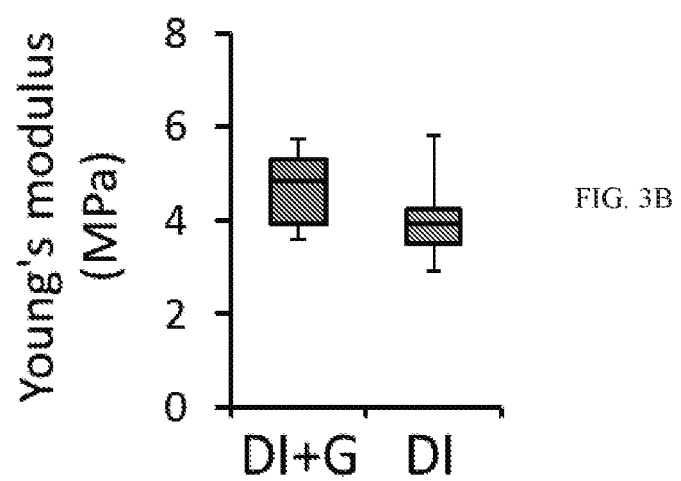
FIG. 3B is a graph showing results of mechanical property, Young's modulus, in decellularized intestine alone (DI) or in decellularized tissue loaded with aptamer-functionalized hydrogel (DI+G)
Figure 3C:
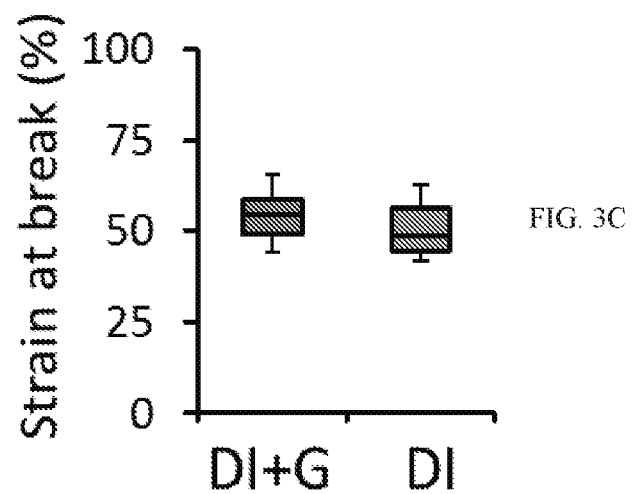
FIG. 3C is a graph showing results of mechanical property, strain at break, in decellularized intestine alone (DI) or in decellularized tissue loaded with aptamer-functionalized hydrogel (DI+G)

Results of experiments to test the peak stress, Young's modulus and strain at break are shown in FIGS. 3A, 3B and 3C.

FIG. 3A is a graph showing results of mechanical property, peak stress, in decellularized intestine alone (DI) or in decellularized tissue loaded with aptamer-functionalized hydrogel (DI+G). The decellularized intestine was cut into rectangular strips with dimensions of 5 mm×30 mm. After the decellularized intestine was fixed by clips, the thickness of the sample was measured using a digital caliper. During the test, the samples were pulled at a rate of 500 mm/min and elongated to a failure. Values were converted to stress-strain curves and the initial modulus was calculated from the initial gradient of the resulting curves (0-10% elongation).

FIG. 3B is a graph showing results of mechanical property, Young's modulus, in decellularized intestine alone (DI) or in decellularized tissue loaded with aptamer-functionalized hydrogel (DI+G).

FIG. 3C is a graph showing results of mechanical property, strain at break, in decellularized intestine alone (DI) or in decellularized tissue loaded with aptamer-functionalized hydrogel (DI+G).

Tissue regeneration compositions described herein provide effective sequestration and sustained release of active agents bound to aptamers attached to hydrogel in the compositions.

The gelatin-aptamer solution is mixed with poly(ethylene glycol) diacrylate (PEGDA). Ten µL of this mixture is applied to 20 mg of the lyophilized decellularized intestine to form the semi-synthetic tissue construct (composite). These composites are transferred to a 15 ml centrifuge tube for washing using double-distilled water (ddH$_2$O). The composites made of decellularized intestine and gelatin-aptamer hydrogel (DI+G) are frozen in a −80° C. freezer for 2 hours and then the DI+G composite is freeze dried for 24 hours in a petri dish and kept in a −20° C. freezer until use. In preparation for use, the DI-gelatin-aptamer semi-synthetic construct (composite) is put into a 10 ml centrifuge tube and 20 µL of 10 µg/mL VEGF solution is spread onto the surface of the construct. The surface solution is allowed to permeate into the construct before continuing the VEGF loading. The centrifuge tubes are re-capped and placed in a 4° C. refrigerator overnight. To assay VEGF release, put the composites are put into release medium (0.1% bovine serum albumin in phosphate buffered saline). Aliquots of the release medium are collected at different times and the amount of VEGF released is quantified by ELISA.

Figure 4A:
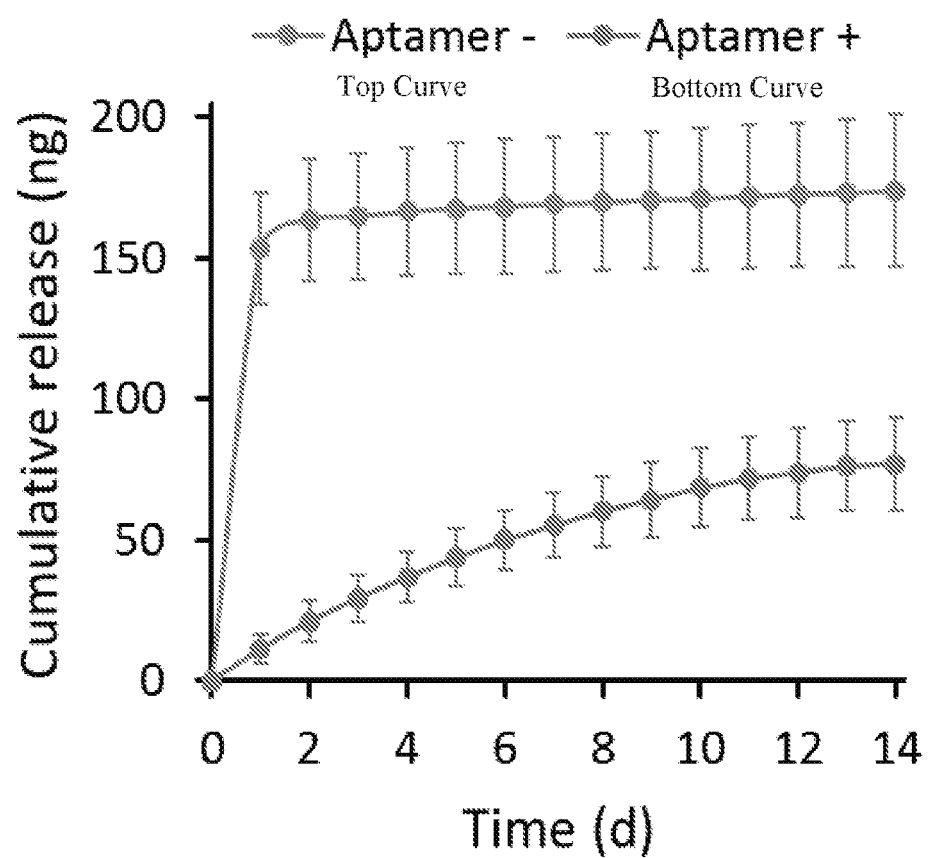
FIG. 4A is a graph showing sustainable release of VEGF from preparations of decellularized tissue loaded with VEGF-containing VEGF-specific-aptamer-functionalized hydrogel compared to preparations of decellularized tissue loaded with VEGF-containing hydrogel without VEGF-specific aptamers.

Results of tests to measure release of active agent VEGF reversibly bound to aptamers in the compositions are shown in FIG. 4A. FIG. 4A is a graph showing sustainable release of VEGF from decellularized intestine (DI) functionalized with VEGF-loaded aptamer-functionalized hydrogel compared to decellularized DI functionalized with VEGF-loaded hydrogel without aptamers.

Figure 4B:
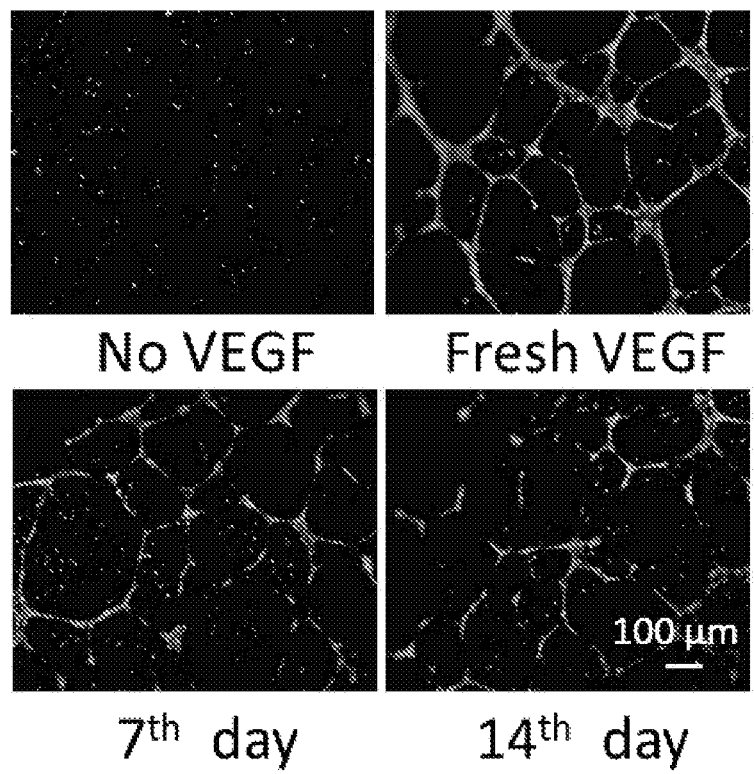
FIG. 4B is a set of images showing stimulation of VEGF on cell tube formation.
Figure 4C:
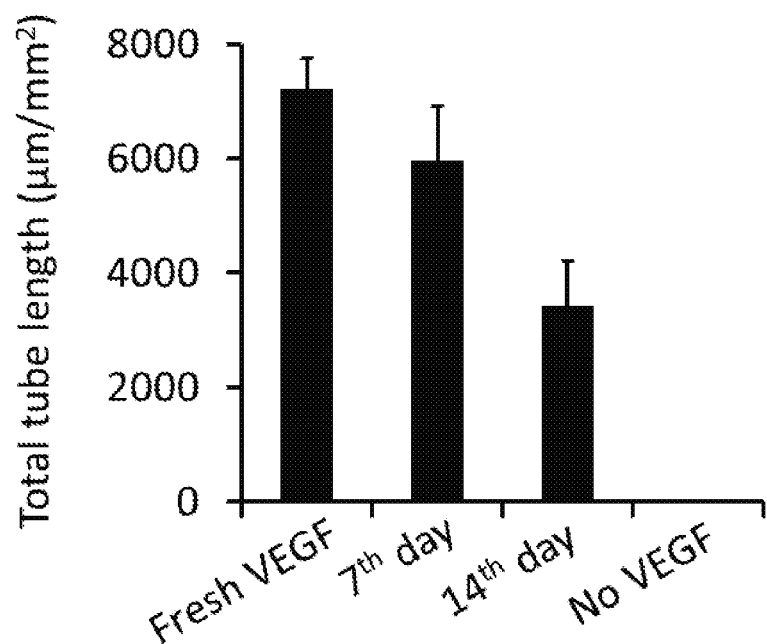
FIG. 4C is a graph showing quantification of cell tube formation.

Results of tests to measure bioactivity of released VEGF are shown in FIGS. 4B and 4C.

For this assay, 4×10$^4$ human umbilical vein endothelial cells (HUVEC) are cultured on a commercially available extracellular matrix product, Geltrex. The cells are treated with M200 medium supplemented with no VEGF, VEGF released from day 7, VEGF released from day 14, or fresh VEGF. After 6 hours, cells are stained with Calcein AM and imaged with a fluorescent microscope. Calcein AM stains the live endothelial cell structure which facilitates imaging and observation of the tube structure of endothelial cells. The formation of tubes indicates that the released VEGF is bioactive. The tube length is quantified by ImageJ. Tube length means the total branch length of the tube structure formed. Endothelial cells form capillary like structure when they are exposed to VEGF or other angiogenic growth factors. This is the indication of bioactivity of released growth factor. If the released growth factor lost its bioactivity, it would not induce tube structure formation.

FIG. 4B is a set of images showing stimulation of VEGF on cell tube formation. Human umbilical vein endothelial cells were cultured on Geltrex and then stimulated with culture medium supplemented with no VEGF, VEGF released at day 7, VEGF released at day 14 or fresh VEGF for 6 hours. Cells were stained with Calcein green and imaged with a fluorescent microscope.

FIG. 4C is a graph showing quantification of cell tubes. The length of the tubes in the images was quantified by ImagJ software.

Tissue regeneration compositions support cell adhesion and cell proliferation. Results of tests to measure cell adhesion on tissue regeneration compositions described herein are shown in FIGS. 5A, 5B, and 5C.

For this cell adhesion assay, decellularized small intestine is cut into 5 mm×5 mm and washed with 2% serum supplemented M200 medium for 1 hour. The decellularized tissue is transferred to a 48 well plate. The cells are washed with 2% serum supplemented M200 medium for three times and diluted to a concentration of 1.0×10$^5$ cells/mL. 250 µL of cell solution (total number: 2.5×10$^4$ HUVEC) is added into each well for incubating with decellularized tissue and decellularized tissue loaded with aptamer functionalized gelatin (20 mg) overnight. The decellularized small intestine is taken out and washed with 2% serum supplemented M200 medium for another three times, followed by the imaging with a fluorescence microscope. Decellularized intestine without cell loading is used as control. HUVECs are stained Vybrant DiD for 30 min and harvested to a 2% serum supplemented M200 medium. This dye was used to stain cells. Using this dye will avoid the auto-fluorescence from the decellularized tissue. This shows that cells adhere to the DI+G hydrogel.

Figures 5A, 5B, 5C:
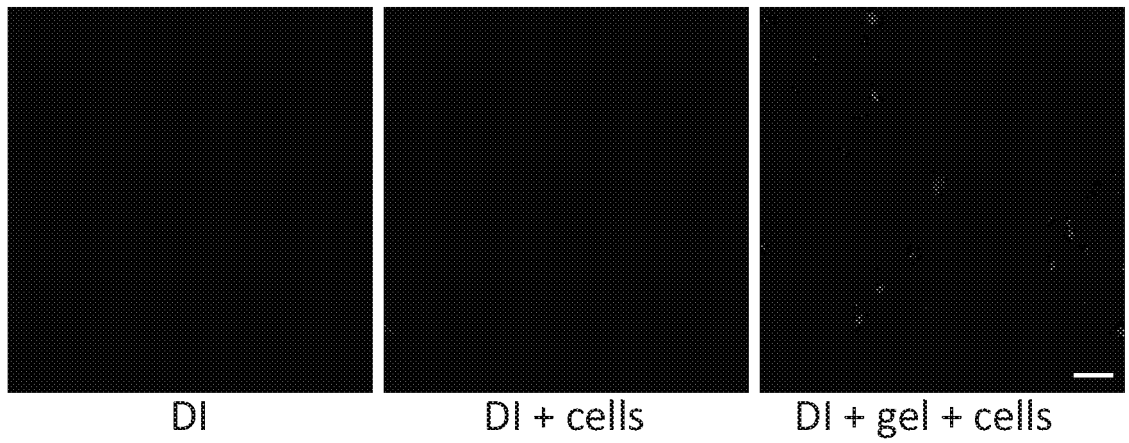
FIG. 5A is an image showing background fluorescence only in a preparation of decellularized small intestine tissue (DI) without cells and without VEGF-containing VEGF-specific-aptamer-functionalized hydrogel.
FIG. 5B is an image showing fluorescence in a preparation of decellularized small intestine tissue with cells (DI+cells) and without aptamer-functionalized hydrogel.
FIG. 5C is an image showing fluorescence in a preparation of decellularized small intestine tissue with cells and with VEGF-containing VEGF-specific-aptamer-functionalized hydrogel (DI+gel+cells)

FIG. 5A is an image showing background fluorescence only in a preparation of decellularized small intestine tissue (DI) without cells and without VEGF-containing VEGF-specific-aptamer-functionalized hydrogel. DI was stained by Vybrant DiD FIG. 5B is an image showing fluorescence in a preparation of decellularized small intestine tissue with cells (DI+cells) and without aptamer-functionalized hydrogel. The DI and cells were stained by Vybrant DiD.

FIG. 5C shows the image of cells growing on DI functionalized with VEGF-loaded aptamer-functionalized hydrogel (DI+gel+cells). The DI+gel composite and cells were stained by Vybrant DiD.

For this cell proliferation assay, 2.5×10$^4$ HUVECs are seeded on the decellularized intestine loaded with VEGF-containing VEGF-specific-aptamer-functionalized hydrogel (DI+G) in a 48 well cell culture plate with M200 medium supplemented with 2% low serum growth supplement for different days. MTS cell proliferation assay is performed at day 1, 3, 7, and 14. DI+G without cell loading is used as control.

Figure 5D:
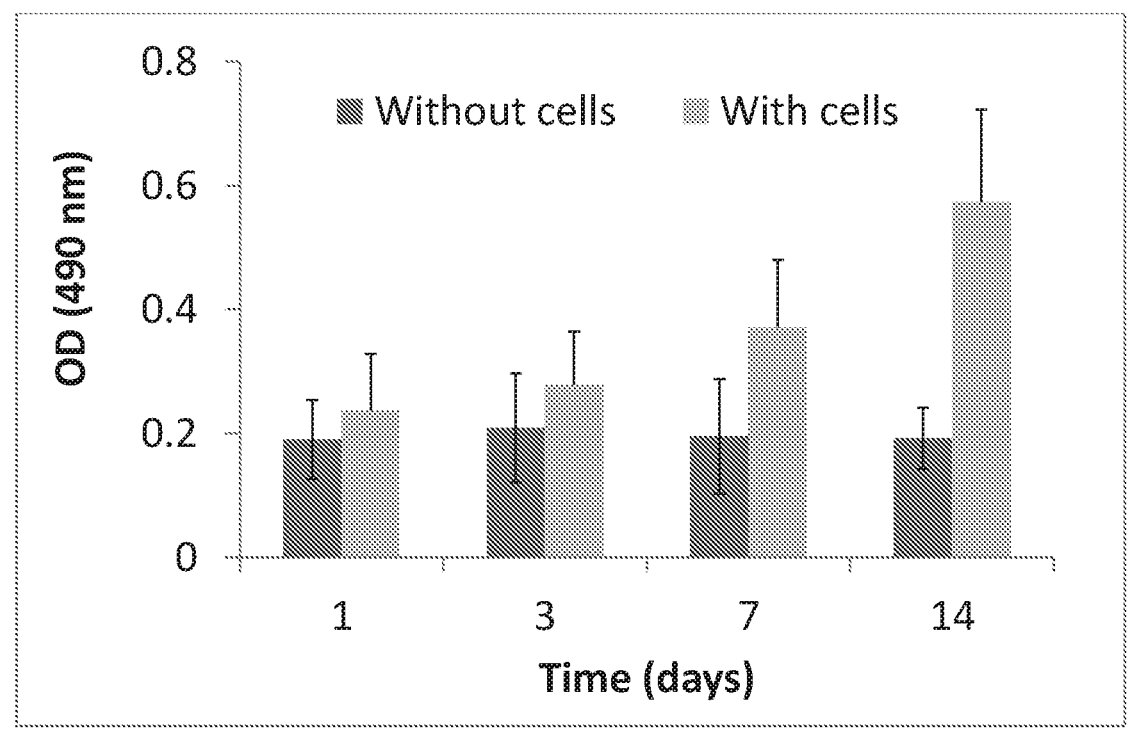
FIG. 5D is a graph showing proliferation of cells in a preparation of decellularized small intestine tissue with VEGF-containing VEGF-specific-aptamer-functionalized hydrogel, a control preparation of decellularized small intestine tissue with aptamer-functionalized hydrogel without any cells is shown for comparison.

Results of tests to measure cell proliferation on tissue regeneration compositions described herein are shown in FIG. 5D.

FIG. 5D is a graph showing proliferation of cells on DI functionalized with VEGF-loaded aptamer-functionalized hydrogel (DI+gel+cells). At different days, MTS assay was performed to test the number of HUVECs in the DI functionalized with VEGF-loaded aptamer-functionalized hydrogel. The same material without cell seeding was used as control.

In a further example, decellularized porcine small intestine submucosa (SIS) is isolated by physical separation of the SIS from other layers of the small intestine. The decellularized SIS is loaded with VEGF alone, VEGF and fibrin hydrogel, fibrin hydrogel and 50 pmol VEGF-containing VEGF-specific-aptamers or fibrin hydrogel and 100 pmol VEGF-specific-aptamers.

Acrylate-Fibrinogen (Fibrinogen-AA) Synthesis

Make 1 mL 0.1 M sodium bicarbonate solution. Add 10 mg fibrinogen to the 1 mL 0.1 M NaHCO3 and vortex to thoroughly mix the fibrinogen in the solution. Dissolve N-Hydroxysuccinimide-acrylate ester (NHS-AA) into DMSO making a final 200 mg/mL NHS-AA solution. Pipet 50 μL of the NHS-AA solution to the 1 mL fibrinogen solution and incubate the mixture solution in a shaker for 2 hours at 37° C. The total 1050 μL Fibrinogen-AA (fibrinogen-acrylate) solution is transferred to a centrifugal filter (100 kDA) and washed at 14000 g for 3 times to remove unreacted NHS-AA and byproducts. Calculate the final remaining fibrinogen concentration in the solution, typically around 50 mg/mL to 100 mg/mL and aliquot the fibrinogen into different PCR tube. The solutions are froze under −20° C. and thawed at 37° C. upon use.

Conjugate Aptamer to the Fibrinogen-Acrylate

Reduce the 10 nmol S-S-Aptamer with 1000 nmol tris(2-carboxyethyl)phosphine (TCEP) solution. Wash the reduced HS-Aptamer by 10 K spin column for three times (14000 g, 4 min) very quickly at 4° C. and use immediately. Warm Fibrinogen-AA at 37° C. Combine the total 10 nmol reduced aptamer solution with the 3 nmol fibrinogen-AA solution. Add 0.5 nmol TECP solution to the mixture and incubate the total solution at 37° C. for 4 hours. Wash to remove the byproducts and free aptamers in a 100 kDa centrifuge filter. Calculate the final Fibrinogen-Aptamer concentration and freeze it at −20° C. The final concentration typically ranges from 5 mg/mL to 20 mg/mL.

Decellularized Small Intestine Submucosa (SIS) Preparation

Clean the inner side remains with tape water (try to flush away all the visible attachments and soak it into water for around 10 min). Cut the small intestine (SI) into small pieces and remove all the fat tissues. Remove the tunica mucosa and tunica muscularis by scrapping. Soak the samples in 3% TRITON X-100™ (2-[4-(2,4,4-trimethylpentan-2-yl)phenoxy]ethanol) overnight. Wash the samples with ddH2O. Soak the samples in 3% SDS overnight in a 4° C. refrigerator. Wash the samples with ddH2O. Soak the samples with 1% w/v penicillin diluted into ddH2O overnight and freeze dry the samples. Store the materials in −20° C. freezer.

SIS+Fibrin Composite Preparation

Punch the freeze-dried SIS into 8 mm diameter disc. Create 13 holes on the SIS with 1 mm diameter biopsy punch. Add 50 μL 10 mg/mL fibrin or 10 mg/mL fibrin-aptamer hydrogel (1 nmol/mL aptamer) to the SIS with holes in a polydimethylsiloxane (PDMS) mold and allow the fibrin hydrogel and fibrin-aptamer hydrogel to solidify at 37° C. for at least 1 hour. Freeze the composite of submucosa+fibrin (SIS+fibrin) hydrogel and composite of submucosa fibrin-aptamer (SIS+fibrin-aptamer) at −80° C. Lyophilize the composite made of SIS+aptamer-functionalized fibrin hydrogel and composite of SIS+fibrin hydrogeland store the composite of SIS+ aptamer-functionalized fibrin hydrogel and composite of SIS+fibrin hydrogel at −20° C.

VEGF Loaded SIS/Fibrin Preparation

Put the lyophilized composite made of SIS+ aptamer functionalized fibrin hydrogel or control composites into a sterile centrifuge tube with the fibrin side up. VEGF solution is directly added into the composites. Incubate the composite with VEGF overnight at 4° C.

Figure 6:
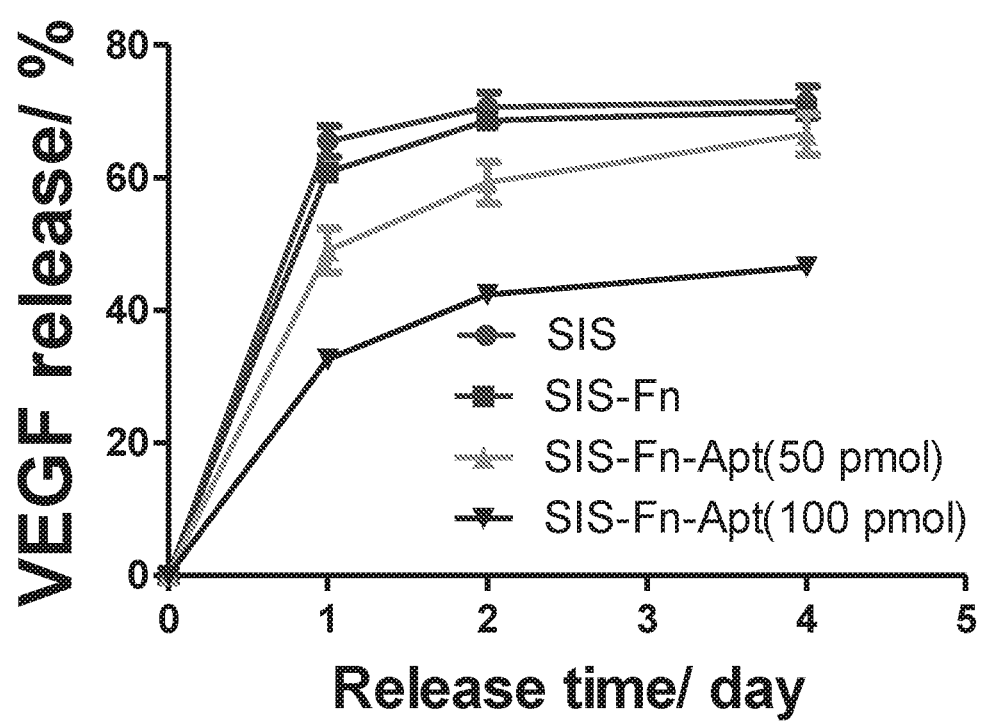
FIG. 6 is a graph showing VEGF release over time from decellularized small intestine submucosa (SIS) loaded with VEGF alone, from SIS loaded with VEGF and fibrin hydrogel, from SIS loaded with fibrin hydrogel and 50 pmol VEGF-containing VEGF-specific-aptamers (VEGF-containing VEGF-specific-aptamer-functionalized fibrin hydrogel) and from SIS loaded with fibrin hydrogel and 100 pmol VEGF-specific-aptamers (VEGF-containing VEGF-specific-aptamer-functionalized fibrin hydrogel)

FIG. 6 is a graph showing VEGF release from VEGF-loaded decellularized small intestine submucosa (SIS), from VEGF-loaded SIS functionalized with fibrin hydrogel (SIS-Fn), from VEGF-loaded SIS functionalized with aptamer-conjugated fibrin hydrogel (SIS-Fn-Apt). The aptamer amount in the SIS-Fn-Apt samples was either 50 pmol or 100 pmol. The amount of VEGF was 200 ng for each group. The amount of released VEGF was quantified by ELISA.

In Vivo Application Example

A sterile 8 mm biopsy punch is used to create an excisional wound on the dorsal midline. The SIS/fibrin-control DNA hydrogel loaded with VEGF (SIS-Fn-DNA+VEGF) or SIS-Fibrin-aptamer hydrogel loaded with VEGF (SIS-Fn-Apt+VEGF) are implanted on the wound. Wound size is imaged by a camera to calculate the macroscopic healing speed at day 0, 1, 3, 5, 7, 9, 11, and 13. The wound healing speed is calculated by comparing with the wound size at day 0. Mice are sacrificed at predetermined time points (e.g., 13 days). The skin of the back is removed using surgical scissors and the wound site is isolated via an 8 mm biopsy punch. Half of the tissue is fixed in paraformaldehyde and half of the tissue is snap-frozen in liquid nitrogen and stored at −80° C. for further analysis.

Figure 7A:
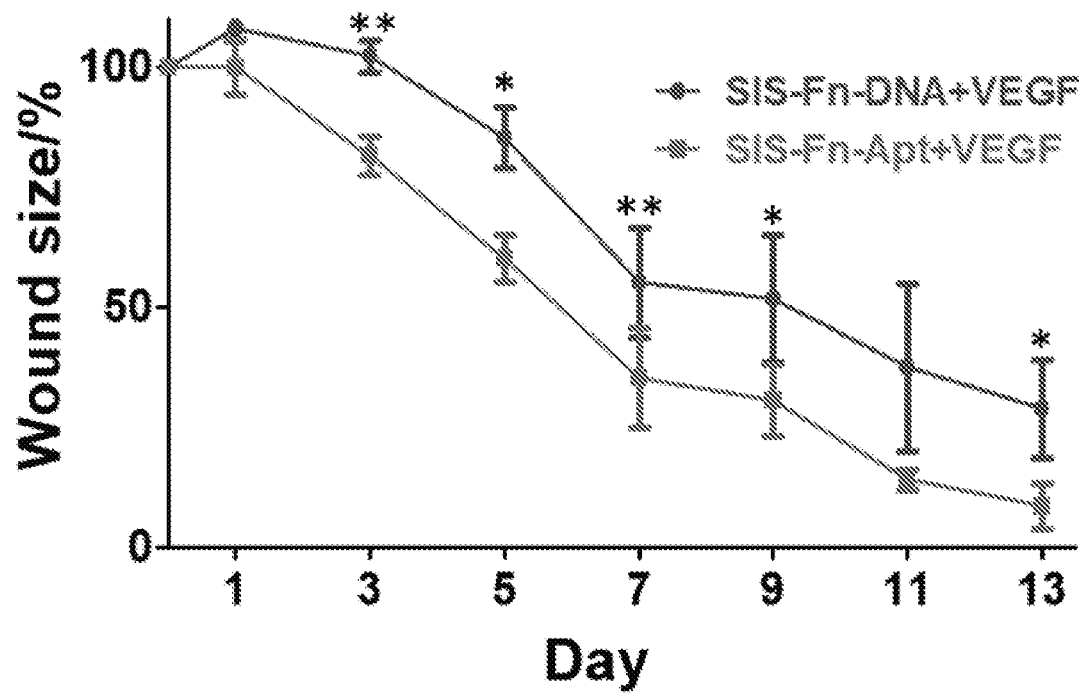
FIG. 7A is a graph showing decrease of skin wound size in vivo over time of animals treated with SIS loaded with VEGF and fibrin (Fn) hydrogel and random DNA oligonucleotides or SIS loaded with VEGF and VEGF-specific aptamer-functionalized fibrin hydrogel.

FIG. 7A is a graph showing the change of skin wound sizes of mice treated with two different composites. Top profile (SIS-Fn-DNA+VEGF): VEGF-loaded SIS functionalized with control aptamer-conjugated fibrin hydrogel; bottom profile (SIS-Fn-Apt+VEGF): VEGF-loaded SIS functionalized with aptamer-conjugated fibrin hydrogel. Dorsal skin wound of 8 mm diameter was created on the back of each mouse. The composite was applied on top of the wound bed and covered with a transparent Tegaderm. At different days, the wound images were taken by a digital camera and quantified by ImageJ software. The size of wound at different days was normalized to the initial wound size. (**=$p<0.01$; *=$p<0.05$; n=4; Paired student t-test).

Figure 7B:
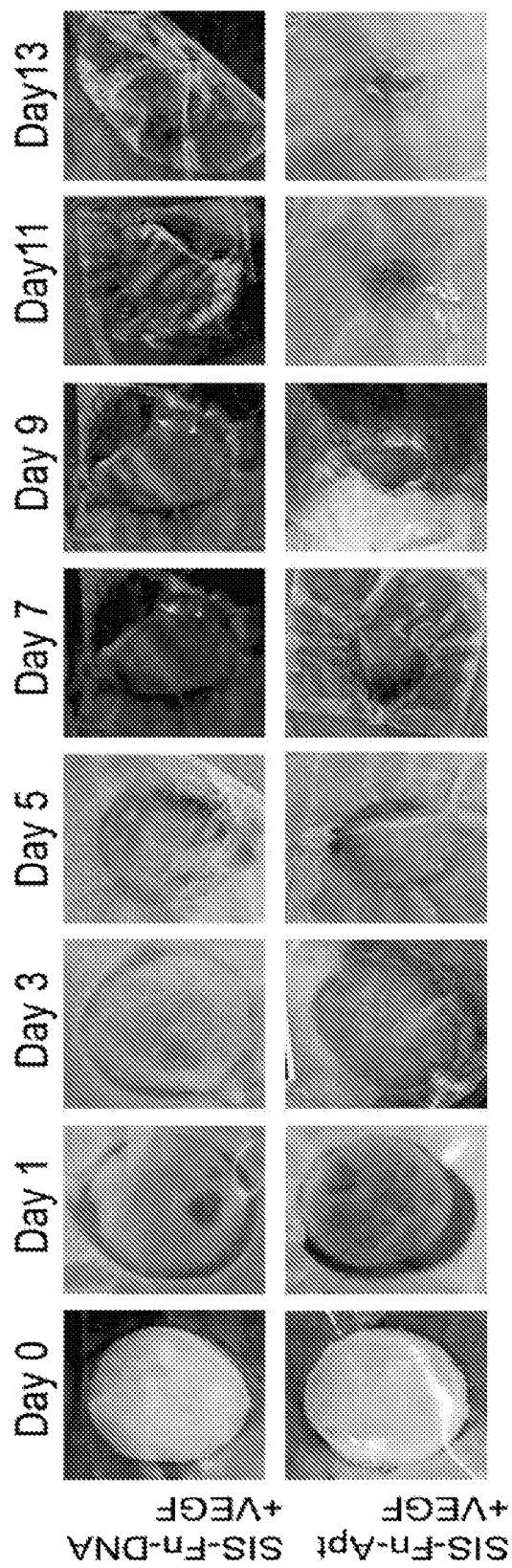
FIG. 7B shows images of decrease of skin wound size in vivo over time of animals treated with SIS loaded with VEGF and fibrin hydrogel and random DNA oligonucleotides or SIS loaded with VEGF and VEGF-specific-aptamer-functionalized fibrin hydrogel (**=$p<0.01$; *=$p<0.05$; n=4; Paired student t-test).

FIG. 7B shows representative images of skin wounds treated with either (SIS-Fn-DNA+VEGF) or (SIS-Fn-Apt+VEGF).

Items

Item 1. A tissue regeneration composition, comprising: a biocompatible porous composite of a decellularized tissue and an aptamer-functionalized hydrogel, wherein the aptamers of the aptamer-functionalized hydrogel specifically and reversibly bind to an active agent.

Item 2. The composition of item 1, further comprising the active agent specifically and reversibly bound to the aptamers.

Item 3. The composition of item 1 or 2, wherein the decellularized tissue is loaded to less than 100% capacity with the aptamer-functionalized hydrogel.

Item 4. The composition of any of items 1 to 3, wherein the decellularized tissue is loaded to between 10% and 75% capacity with the aptamer-functionalized hydrogel.

Item 5. The composition of any of items 1 to 4, wherein the decellularized tissue is loaded to between 20% and 50% capacity with the aptamer-functionalized hydrogel.

Item 6. The composition of any of items 1 to 5, wherein the decellularized tissue is a decellularized mammalian tissue.

Item 7. The composition of any of items 1 to 6, wherein the aptamer-functionalized hydrogel comprises an aptamer-functionalized biological polymer.

Item 8. The composition of any of items 1 to 7, further comprising an adjunct therapeutic agent and/or stem cell.

Item 9. The composition of any of items 1 to 8, further comprising a support in contact with the biocompatible porous composite.

Item 10. The composition of any of items 1 to 9, wherein the aptamer-functionalized hydrogel comprises more than one type of aptamer, wherein each type of aptamer specifically and reversibly binds to a different active agent.

Item 11. A method of aiding tissue regeneration in a subject in need thereof, comprising: administering a tissue regeneration composition according to any of items 1 to 10 to the subject in need thereof.

Item 12. The method of item 11, wherein the subject has a wound and the administering comprises contacting the wound with the tissue regeneration composition.

Item 13. The method of item 11 or 12, wherein the tissue is skin.

Item 14. The method of item 11 or 12, wherein the tissue is a tissue is an internal tissue.

Item 15. The method of item 11 or 12, wherein the internal tissue is a tissue of an internal organ.

Item 16. A method of producing the tissue regeneration composition of any of items 1 to 10, comprising: loading a decellularized tissue with a precursor solution, the precursor solution comprising at least one aptamer-functionalized component; and polymerizing the precursor solution in situ in the decellularized tissue, thereby producing the tissue regeneration composition of any of items 1 to 10.

Item 17. The composition of any of items 1 to 10, or method of any of items 11 to 16, wherein the aptamers of the aptamer-functionalized hydrogel are nucleic acid aptamers.

Item 18. The composition of any of items 1 to 10, or method of any of items 11 to 17, wherein the aptamers of the aptamer-functionalized hydrogel are nucleic acid aptamers which specifically and reversibly bind to an active agent selected from the group consisting of: VEGF, PDGF, a bone morphogenetic protein, brain-derived neurotrophic factor, ciliary neurotrophic factor, epidermal growth factor, erythropoietin, fibroblast growth factor, glial cell line-derived neurotrophic factor, granulocyte-macrophage colony-stimulating factor, granulocyte macrophage colony-stimulating factor, growth differentiation factor-9, hepatocyte growth factor, hepatoma-derived growth factor, insulin-like growth factor, keratinocyte growth factor, migration-stimulating factor, myostatin, a neurotrophin, nerve growth factor, neurotrophin 3, neurotrophin 4, neurotrophin 5, thrombopoietin, T-cell growth factor, transforming growth factor alpha, transforming growth factor beta, tumor necrosis factor-alpha, placental growth factor, an interleukin, IL-1, IL-2, IL-3, IL-4, IL-5, IL-6 and IL-7.

Item 19. The composition of any of items 1 to 10, or method of any of items 11 to 17, wherein the aptamers of the aptamer-functionalized hydrogel include two or more types of nucleic acid aptamers wherein each type of nucleic acid aptamer specifically and reversibly binds to an active agent selected from the group consisting of: VEGF, PDGF, a bone morphogenetic protein, brain-derived neurotrophic factor, ciliary neurotrophic factor, epidermal growth factor, erythropoietin, fibroblast growth factor, glial cell line-derived neurotrophic factor, granulocyte-macrophage colony-stimulating factor, granulocyte macrophage colony-stimulating factor, growth differentiation factor-9, hepatocyte growth factor, hepatoma-derived growth factor, insulin-like growth factor, keratinocyte growth factor, migration-stimulating factor, myostatin, a neurotrophin, nerve growth factor, neurotrophin 3, neurotrophin 4, neurotrophin 5, thrombopoietin, T-cell growth factor, transforming growth factor alpha, transforming growth factor beta, tumor necrosis factor-alpha, placental growth factor, an interleukin, IL-1, IL-2, IL-3, IL-4, IL-5, IL-6 and IL-7.

Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A tissue regeneration composition, comprising:
   a biocompatible porous composite of a decellularized tissue and an aptamer-functionalized hydrogel, wherein the aptamers of the aptamer-functionalized hydrogel specifically and reversibly bind to an active agent.

2. The composition of claim 1, wherein the decellularized tissue is loaded to less than 100% capacity with the aptamer-functionalized hydrogel.

3. The composition of claim 1, wherein the decellularized tissue is loaded to between 10% and 75% capacity with the aptamer-functionalized hydrogel.

4. The composition of claim 1, wherein the decellularized tissue is loaded to between 20% and 50% capacity with the aptamer-functionalized hydrogel.

5. The composition of claim 1, wherein the decellularized tissue is a decellularized mammalian tissue.

6. The composition of claim 1, wherein the aptamer-functionalized hydrogel comprises an aptamer-functionalized biological polymer.

7. The composition of claim 1, wherein the aptamer-functionalized hydrogel comprises more than one type of aptamer, wherein each type of aptamer specifically and reversibly binds to a different active agent.

8. The composition of claim 1, wherein the aptamers of the aptamer-functionalized hydrogel are nucleic acid aptamers.

9. The composition of claim 1, wherein the aptamers of the aptamer-functionalized hydrogel are nucleic acid aptamers which specifically and reversibly bind to an active agent selected from the group consisting of: VEGF, PDGF, a bone morphogenetic protein, brain-derived neurotrophic factor, ciliary neurotrophic factor, epidermal growth factor, erythropoietin, fibroblast growth factor, glial cell line-derived neurotrophic factor, granulocyte-macrophage colony-stimulating factor, granulocyte macrophage colony-stimulating factor, growth differentiation factor-9, hepatocyte growth factor, hepatoma-derived growth factor, insulin-like growth factor, keratinocyte growth factor, migration stimulating factor, myostatin, a neurotrophin, nerve growth factor, neurotrophin 3, neurotrophin 4, neurotrophin 5, thrombopoietin, T-cell growth factor, transforming growth factor alpha, transforming growth factor beta, tumor necrosis factor-alpha, placental growth factor, an interleukin, IL-I, IL-2, IL-3, IL-4, IL-5, IL-6 and IL-7.

10. The composition of claim 1, wherein the aptamers of the aptamer-functionalized hydrogel include two or more types of nucleic acid aptamers wherein each type of nucleic acid aptamer specifically and reversibly binds to an active agent selected from the group consisting of: VEGF, PDGF, a bone morphogenetic protein, brain-derived neurotrophic factor, ciliary neurotrophic factor, epidermal growth factor, erythropoietin, fibroblast growth factor, glial cell line derived neurotrophic factor, granulocyte-macrophage colony-stimulating factor, granulocyte macrophage colony-stimulating factor, growth differentiation factor-9, hepatocyte growth factor, hepatoma-derived growth factor, insulin-like growth factor, keratinocyte growth factor, migration-stimulating factor, myostatin, a neurotrophin, nerve growth factor, neurotrophin 3, neurotrophin 4, neurotrophin 5, thrombopoietin, Tcell growth factor, transforming growth factor alpha, transforming growth factor beta, tumor necrosis factor-alpha, placental growth factor, an interleukin, IL-I, IL-2, IL-3, IL-4, IL-5, IL-6 and IL-7.

11. The composition of claim 1, further comprising the active agent bound to the aptamers in a reversible manner.

12. The composition of claim 1, further comprising an adjunct therapeutic agent and/or stem cell disposed in contact with the biocompatible porous composite.

13. The composition of claim 1, further comprising a support in contact with the biocompatible porous composite.

14. A method of aiding tissue regeneration in a subject in need thereof, comprising:
   administering a tissue regeneration composition according to claim 1 to the subject in need thereof.

15. The method of claim 14, wherein the subject has a wound and the administering comprises contacting the wound with the tissue regeneration composition.

16. The method of claim 14, wherein the tissue is skin.

17. The method of claim 14, wherein the tissue is an internal tissue.

18. The method of claim 17, wherein the internal tissue is a tissue of an internal organ.

19. A method of producing the tissue regeneration composition of claim 1, comprising:
   loading a decellularized tissue with a precursor solution, the precursor solution comprising at least one aptamer-functionalized component capable of forming the aptamer-functionalized hydrogel upon polymerization of the precursor solution; and
   polymerizing the precursor solution in situ in the decellularized tissue, producing aptamer-functionalized hydrogel in contact with the decellularized tissue, thereby producing the tissue regeneration composition.

* * * * *